United States Patent [19]

Klinvex et al.

[11] Patent Number: 4,642,215

[45] Date of Patent: Feb. 10, 1987

[54] UNIVERSAL TOOL FOR ULTRASONIC TESTING OF NUCLEAR REACTOR VESSELS

[75] Inventors: Daniel E. Klinvex, McKeesport; Suzanne B. Crusi, Hempfield Township, Westmoreland County; William E. Kepes, Penn Township, Westmoreland County, all of Pa.; Joseph A. Vano, New Providence, N.J.

[73] Assignee: Westinghouse Electric Corp., Pittsburgh, Pa.

[21] Appl. No.: 541,597

[22] Filed: Oct. 13, 1983

[51] Int. Cl.[4] .................. G21C 17/00; G01N 29/04
[52] U.S. Cl. ..................................... 376/249; 73/641
[58] Field of Search ................. 376/249, 252; 73/628, 73/641

[56] References Cited

U.S. PATENT DOCUMENTS

| | | | |
|---|---|---|---|
| 3,934,457 | 1/1976 | Clark et al. | 376/249 |
| 3,943,756 | 3/1976 | Aubert et al. | 376/249 |
| 4,170,891 | 10/1979 | Elswer | 73/641 |
| 4,196,049 | 4/1980 | Burns et al. | 376/249 |

Primary Examiner—Salvatore Cangialosi
Attorney, Agent, or Firm—L. A. DePaul

[57] ABSTRACT

A universal tool for the weld inspection of tubular objects such as reactor vessels is disclosed. The tool is constructed from an array of transducers mounted in groups for common inspection of a particular weld volume. The individual transducers, as well as the groups, are arranged in a compact assembly for minimizing the overall dimensions of the tool and its corresponding weight. The transducers are arranged in a manner which permits inspection of tubular objects having different radii of curvature and corresponding different diameters with a single tool without the need of having to individually adjust the orientation angles of the transducers.

21 Claims, 4 Drawing Figures

UNIVERSAL TOOL FOR ULTRASONIC TESTING OF NUCLEAR REACTOR VESSELS

BACKGROUND OF THE INVENTION

The present invention relates in general to a universal tool for inspecting objects such as composite tubular objects and the like for locating various defects therein, and more particular, to a universal tool having a compact array of ultrasonic transducers arranged for the testing of various welds of such tubular objects, such as nuclear reactor vessels and components thereof, having different radii of curvature for detection of weld defects therein, for example, cracks, voids and the like.

Nuclear reactor vessels used in the commercial generation of electrical power are of two types, namely, the pressurized and boiling water type. In either case, the reactor vessel is constructed of a generally cylindrical metallic shell having a base and top flange welded thereto. The main shell portion itself is usually constructed of a series of lesser cylinders welded to each other along circumferential and longitudinal seams. In addition, a plurality of circumferentially spaced nozzles extend through the main shell and are likewise welded to the shell wall. Thus, numerous welds are necessarily used in fabricating the reactor vessel, in securing the top flange to the main shell, and in securing various injection inlet and outlet nozzles to the wall of the cylindrical shell of the reactor vessel. Typically, these welds are referred to as top flange welds, nozzle welds, nozzle safe end welds, ligament areas, i.e., the area between the stud holes of the top flange, circumferential welds and longitudinal welds.

These numerous welds, in particular their weld area and/or volume are, of course, inspected prior to the reactor vessel's initial use. Such inspection is carried out with all portions of the reactor vessel relatively accessible to an inspection tool or tools prior to its permanent installation. However, in-service inspection of the reactor vessel weld area and/or volume is not only desirable, but is mandated under certain government regulations. Under such regulations, it is required that each of the reactor vessel weld volumes be subjected to periodic volumetric examination whereby the structual integrity of the vessel is monitored. As required by such regulations, the top flange welds, nozzle welds, nozzle safe end welds and ligament areas are to be inspected at forty month periods, while the inspection of the circumferential and longitudinal welds of the vessel are conducted at ten year periods. To this end, there is disclosed in U.S. Pat. Nos. 4,196,049 and 4,170,891, which patents are assigned to the same assignee of the present invention, a tool for use in connection with making such inspections and which includes an ultrasonic transducer array for conducting the examination of the various weld volumes of the reactor vessel and its component parts at the forty month and ten year periods.

The foregoing prior art transducer array or tool is generally comprised of a relatively large rectangular support plate, typically 26 inches by 18 inches, having a plurality of individual ultrasonic transducers movably mounted thereon. The transducers, which include an ultrasonic transmitter and receiver, are each mounted to the support plate between a pair of outwardly extending guide rails which permit for the adjustable positioning of the transducers relative to one another on the support plate. In addition, the transducers are individually adjustable for emitting an ultrasonic beam at a predetermined angle relative to the support plate for penetrating the weld volume to be inspected at an angle mandated by the government regulations. Typically, the inspection angles required by these regulations are nominal angles of 45° and 60° with respect to a perpendicular to the examination surface, however, a tolerance of ±2° is generally permitted.

In order to obtain the correct inspection angle for each of the ultrasonic transducers when inspecting a specific reactor vessel, it has been the prior art practice that each such transducer be individually positioned and that its orientation angle with respect to the support plate be individually adjusted prior to conducting an examination. In this manner, the transducers of the foregoing tool have been randomly positioned at a variety of individually calculated angles in order to meet the government regulations. However, such random positioning of these transducers has resulted in the need for a relatively large support plate which has rendered inspection of various reactor vessels cumbersome by the inability of the support plate to be manipulated effectively within the reactor vessel being inspected, as well its component parts, such as the attached nozzles. Further, the added weight of the support plate resulting from its size has further hindered the ability to effective manipulate the prior art tool in an optimum manner.

In addition to the undesirable size and weight of the prior art tool, such tool could not be used directly for inspection of reactor vessels and nozzles of different size, that is, those having different radii of curvature. For example, there is generally known three sizes of nuclear reactor vessels commonly referred to as the two-loop, three-loop and four-loop vessel and such vessels typically have different internal diameters, for example, diameters of 132 inches, 155 inches and 172 inches. As the examination surface of each of these reactor vessels have a different radius of curvature, it has been required that the orientation angles and position of the plurality of individual transducers of the prior art tool be individually adjusted for the weld inspection of each reactor vessel or component part having a different diameter. For example, a separate tool has been provided for the inspection of reactor vessels at the forty month period and one for the ten year period.

In using such tools, the relative position of the transducers has required adjustment via the guide rails, as well as adjusting their orientation angle relative to the support plate in order to accommodate the diameter of the reactor vessel being examined and the corresponding radius of curvature of the examination surface. Unless such repositioning and alignment of the individual transducers were performed, these prior art tools could not inspect reactor vessels of varing diameter while meeting the government regulations, for example, having nominal inspection angles of 45° and 60°. Although the precise location of the individual transducers and their orientation angles with respect to the support plate can be determined by computer analysis, it has been required that these transducers be individually positioned and aligned by hand. This hand positioning and alignment of the individual transducers often consumed as much as two man days resulting in inefficient use of the prior art tool, as well as additional expense when performing inspection of reactor vessels of different size.

Accordingly, it can be appreciated that there is an unsolved need for a universal tool for inspecting tubular objects such as vessels and the like, in particular, reactor vessels and their component parts, for locating various defects such as cracks and voids in the various weld volumes while being independent of the reactor vessel size, and while still meeting government regulations mandated for such testing.

SUMMARY OF THE INVENTION

It is broadly an object of the present invention to provide a universal tool for ultrasonic testing of various objects such as tubular objects and the like, and in particular, nuclear reactor vessels and their component parts, such as nozzles and flanges, which overcomes or avoids one or more of the foregoing disadvantages resulting from the above-mentioned prior art tool, and which fullfills the specific requirements for such a tool, as specifically mandated by government regulations. Specifically, it is within the contemplation of one aspect of the present invention to provide a universal tool for ultrasonic weld testing of nuclear reactor vessels, remotely in an underwater radioactive environment, from inside the reactor vessel, and which ultrasonic testing meets all government regulations.

A further object of the present invention is to provide a universal tool for ultrasonic testing of reactor vessels, wherein such tool is of minimum size and weight so as to faciliate its manipulation within the reactor vessel and its associated nozzles.

A still further object of the present invention is to provide a universal tool for ultrasonic testing of reactor vessels wherein a predetermined weld volume may be inspect simultaneously by a plurality of transducers.

A yet still further object of the present invention is to provide a universal tool for ultrasonic weld testing of reactor vessels wherein the individual transducers are positioned and aligned for common inspection of vessels having different diameters and examination surfaces having corresponding different radii of curvature.

A yet still further object of the present invention is to provide a universal tool for ultrasonic weld testing of reactor vessels which is adapted for use for inspecting such vessels of various size and corresponding different radii of curvature at a minimum of set-up time and a reduction of the associated economic expense.

In accordance with one embodiment of the present invention there is provided a composite tool for inspecting portions of an object for locating defects therein. The composite tool is constructed of a support plate, and a plurality of individual sensors mounted to the plate in a group for inspecting portions of the object, the sensors being positioned relative to one another so as to minimize the distance therebetween and aligned at predetermined angles to the plate to permit simultaneous inspection of a predetermined portion of the object when the plate is positioned at a predetermined location relative to the object.

Further in accordance with the above embodiment, the sensors are arranged in a plurality of groups, each group adapted for inspection of a different predetermined portion of the object and wherein the groups of individual sensors are positioned relative to one another so as to minimize the size of the plate.

In accordance with another embodiment of the present invention, there is provided a composite tool for inspecting portions of a plurality of objects for locating defects therein, each of the objects having a longitudinal axis and a corresponding different radius of curvature. The composite tool is constructed of a support plate, and a plurality of individual sensors mounted to the plate for emitting inspection beams therefrom, the sensors being arranged relative to the plate such that the inspection beams penetrate a predetermined portion of the object lying substantially along an imaginary line indicated on the surface of the object when the plate is positioned at a predetermined location relative to the line, the imaginary line lying in a plane containing the longitudinal axis of the body, whereby the inspection of the predetermined portion of the object by the sensors is independent of the radius of curvature of the object being inspected.

Further in accordance with the last mentioned embodiment, the sensors are arranged along an axis of the plate, which during an examination lies in a plane containing the longitudinal axis of the object and the imaginary line when the plate is positioned at a predetermined location relative to the object for inspection thereof, and wherein the sensors are aimed for directing an inspection beam falling within the plane.

Still further in accordance with the last mentioned embodiment, the sensors are arranged along an axis of the plate, which during an examination lies outside the plane containing the longitudinal axis of the object and the imaginary line when the plate is positioned at a predetermined location relative to the object for inspection thereof, and wherein the sensors are aimed for directing an inspection beam intersecting the plane at the imaginary line.

BRIEF DESCRIPTION OF THE DRAWINGS

The above description, as well as further objects, features and advantages of the present invention will be more fully understood by reference to the following detailed description of the presently preferred, but nonetheless, illustrative, universal tool for ultrasonic weld testing of tubular objects such as nuclear reactor vessels, when taken in conjunction with the accompanying drawings, wherein.

DETAILED DESCRIPTION

Prior to a description of the universal tool in accordance with the present invention, it is to be understood that the specific requirements for and manner of inspecting the various weld volumes of a nuclear reactor vessel are governed by Section XI of the ASME Code dealing with ultrasonic examination of reactor pressure vessels, including Article IV entitled Ultrasonic Examination When Dimensioning Of Indications Is Required, as appearing in Section V. In addition to the foregoing government regulations, the universal tool of the present invention is utilized in complying with the various tests and procedures set forth in such regulations, in the general manner described in the foregoing commonly assigned United States patents.

Figure 1:
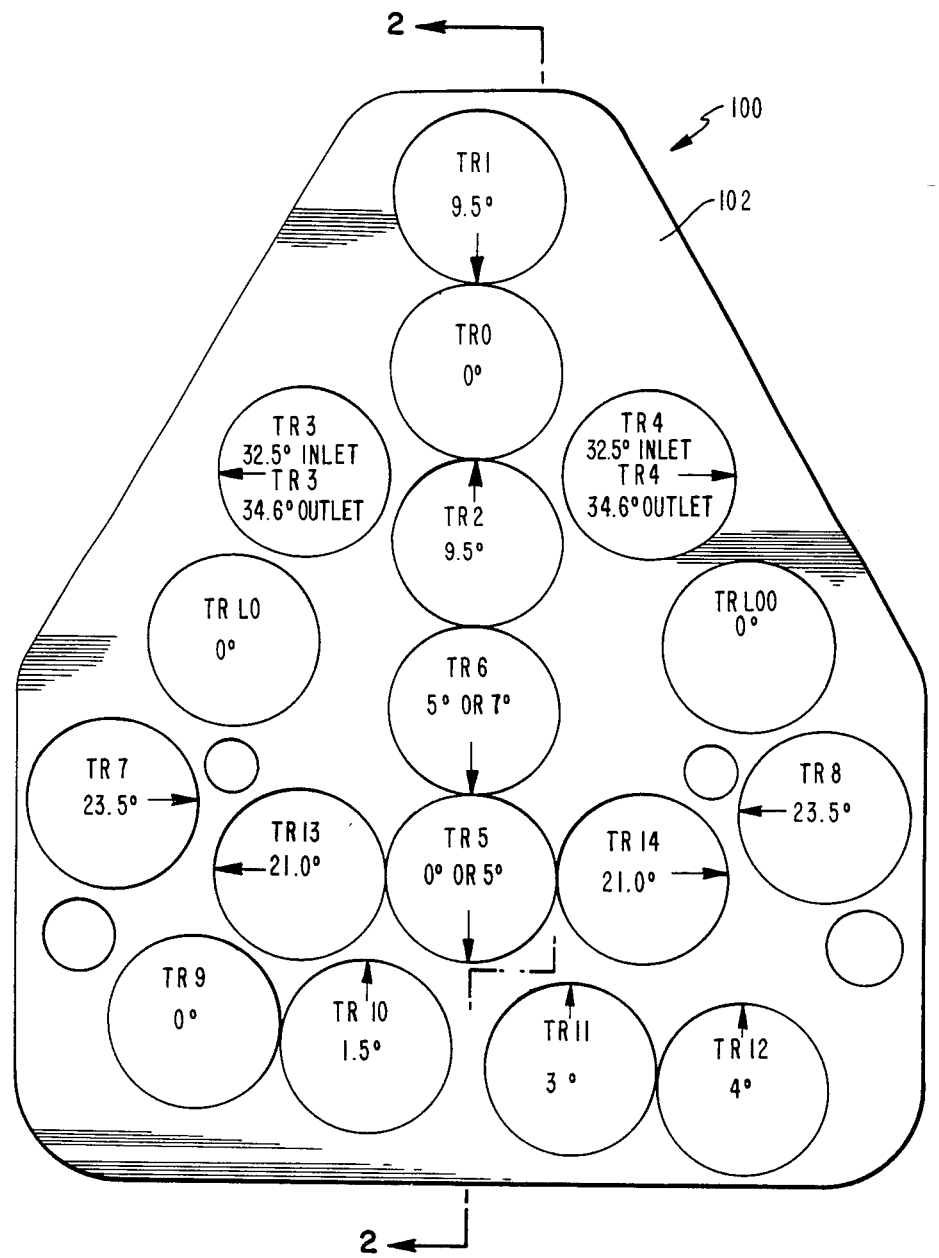
FIG. 1 is a front view of a universal tool constructed in accordance with the present invention adapted for inspection of various welds of a reactor vessel at forty month periods and having the transducers arranged in groups at predetermined positions and at predetermined orientation angles to the support plate for minimizing the size thereof and adapting the tool for use with various size reactor vessels which have different radii of curvature.

Referring now to the drawings, wherein like reference numerals represent like elements, there is shown in FIG. 1 a front view of a universal tool generally designated by reference character 100. The universal tool 100 is adapted for inspecting the various weld volumes of a nuclear reactor vessel which, in accordance with the government regulations, require periodic inspection at forty month intervals. Specifically, these weld volumes are commonly referred to as the top flange to vessel welds, nozzle safe end to vessel welds and ligament areas, e.g., those weld areas between the stud holes on the top flange of the reactor vessel. As shown in FIG. 1, the tool 100 is constructed of a plurality of individual ultrasonic transducers mounted in an array to a support plate 102. The specific manner of mounting the transducers to the support plate 102 will be described hereinafter.

Each of the transducers include an ultrasonic transmitter and receiver combination such that an ultrasonic sensing beam may be emitted from and its reflection received by the same transducer. Each of the transducers are mounted to the support plate 102 for emitting an ultrasonic sensing beam in the direction of its respective illustrated arrow and at an orientation angle to the support plate 102 as designated in FIG. 1 for each of the respective transducers. Where no arrow is designated for a particular transducer, such transducer is arranged for emitting an ultrasonic sensing beam at an angle normal to a plane containing the support plate 102. By way of example, with specific reference to transducer TR 1, such transducer is arranged on the support plate 102 for emitting an ultrasonic sensing beam in a downward direction as indicated by the arrow at an angle of 9.5° to the support plate.

In addition to the transducers being mounted to the support plate for emitting an ultrasonic sensing beam in a particular direction at a particular angle to the support plate, such transducers are arranged in clustered compact groups in accordance with the desired weld volume to be inspected. Specifically, transducers TR 0, TR 2, TR 3 and TR 4 are designed for inspecting the nozzle safe end welds, transducers TR 5, TR 6, TR 7 and TR 8 are designed for inspecting the nozzle to vessel welds, transducers TR 9, TR 10, TR 11 and TR 12 are designed for inspecting the flange to vessel welds, transducers TRL 0 and TRL 00 are designed for inspecting the ligament areas, and transducers TR 13 and TR 14 are designed for insuring proper tool orientation prior to use, that is, verifying that transducer TR 0 has been arranged normal to the examination surface of the object being inspected.

With the individual transducers arranged as close to one another as possible, as well as each group being arranged as close as possible to an adjacent group, the overall size of the support plate 102 may be conveniently reduced to a triangular shaped plate having a longitudinal length of about 16 inches and a base length of about 13¼ inches. This results in a substantially smaller tool 100 and one of lesser weight than that of the prior art. In this regard, the tool 100 of the present invention can be manipulated with greater ease and precision within the reactor vessel for inspection of the numerous weld volumes, as well as requiring manipulation equipment of lighter weight construction and accordingly less cost. The ability to position the individual transducers as close as possible to one another is, in part, achieved by the elimination of the guide rails of the prior art tool, as well as the planed clustering of the individual transducers in groups with respect to the particular weld volume to be examined in accordance with the principles of the present invention.

As previously described, the ASME Code dictates the manner in which reactor pressure vessel welds must be ultrasonically examined. The inspection beam refracted angle within the weld volume being examined is also specified by the ASME Code. The prior art tool employed a technique of mounting the individual transducers in a manner that allowed for variable transducer locations by means of the guide rails and for variable inspection beam origination angles. However, many hours of set-up time was consumed previous to each reactor vessel inspection as beam entry angles and transducer locations had to be calculated for each particular weld volume to be examined. In addition, the tool which includes the support plate for mounting the transducers thereto, was also relatively large and heavy, thereby often leading to reactor vessel interference and transducer array positioning errors. In accordance with the tool 100 of the present invention, the use of high strength aluminum in the construction of the design of the tool, as well as the compact arrangement of the individual transducers in clustered groups, has resulted in a tool of approximately 50% smaller size and 30% lighter weight than the prior art tool.

The universal tool 100, in accordance with the present invention, is designed to eliminate costly transducer array set-up time, while reducing the physical size and weight of the entire assembly, and while keeping within the inspection guidelines set forth by the ASME Code. In accordance with the present invention, the tool 100 results in great savings in transducer array set-up time due to the elimination of the dependence of transducer orientation angle and location, as mandated by the prior art tool, when inspecting reactor vessels of different size and corresponding different radii of curvature. The elimination of such set-up requirements and the possible human error coupled therewith, results in greater repeatable accuracy in the inspection of reactor vessel weld volumes, as well as resulting in an improved commercial product resulting from the foregoing size and weight reductions of the universal tool.

In accordance with the prior art tool, it was required that the orientation angle of the individual transducers be adjusted for each particular weld volume to be examined as the reactor vessel diameter increased along with its corresponding radius of curvature so as to permit for the proper inspection of these weld volumes at inspection beam entry angles as mandated by the ASME Code. This requirement of individual adjusting the transducer orientation angle to accommodate various size reactor vessels, for the most part, is eliminated in accordance with the universal tool of the present invention. In this regard, except for a specified number of transducers, the orientation angle for the transducers mounted to the support plate 102 are maintained constant and independent of the reactor vessel diameter and its corresponding radius of curvature. To this end, the principles of the present invention will be described with respect to FIG. 4.

Figure 4:
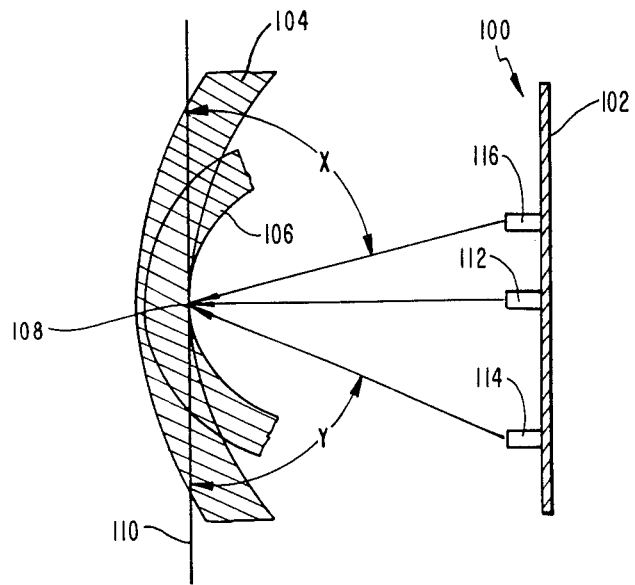
FIG. 4 is a diagrammatic illustration showing the independence of the universal tool with respect to reactor vessels having different diameters and corresponding different radii of curvature.

Turning now specifically to FIG. 4, there is diagrammatically illustrated, in cross-section, a portion of a cylindrical vessel 104 having a first diameter and corresponding radius of curvature and a second vessel 106 having a second diameter and corresponding radius of curvature, which diameter and radius of curvature are substantially smaller than those of the first vessel. The first and second vessels 104, 106 are arranged, in cross-section, to have a portion of their internal surface intersect at a common point designed by reference character 108. Extending through the common point 108, there is drawn a line 110 which is tangent to the radius of curvature of both the first and second vessels 104, 106 at the common point. The universal tool 100 is positioned internally within the first and second vessels 104, 106 having the support plate 102 arranged spaced from and parallel to the tangent line 110. For purposes of illustration only, the universal tool is shown to include three transducers 112, 114, 116.

Transducer 112 is arranged for emitting an ultrasonic sensing beam along the common radius of the first and second vessels 104, 106 and therefore normal to the tangent line 110. This may be achieved by arranging the transducer 112 along the longitudinal axis of the support plate 102 and aligning such longitudinal axis to lie within a plane containing the radial axis of the first and second vessels 104, 106 or alternatively moving the tool parallel to the tangent line 110 to effect such alignment. In other words, the transducer 112 is arranged such that the emitted ultrasonic sensing beam lies within a plane containing the radial axis of the vessels 104, 106 and therefore normal to the tangent line 110. The foregoing may also be explained in that the transducer 112 is arranged relative to the support plate 102 such that the ultrasonic sensing beam emitted from the transducer penatrates a predetermined portion of the vessels 104, 106 at a location lying substantially along an imaginary line on the surface of these vessels extending through the common point 108 and parallel to the longitudinal axis of the vessels when the plate is positioned at a predetermined location relative to the imaginary line.

From the foregoing explanation, a plurality of transducers, such as transducer 112, may be arranged on the support plate 102 along a common line, such as the longitudinal axis, which line falls within a plane containing the radial axis of the vessels 104, 106 whereby the ultrasonic sensing beams emitted therefrom are received by the reactor vessel normal to the tangent line 110. In accordance with this arrangement of transducers and the support plate 102, the ultrasonic sensing beams emitted from such transducers will penetrate the vessels 104, 106 along an imaginary line lying within a plane containing the radial axis for such vessels and normal to the tangent line 110, and therefore being independent of the radius of curvature of either vessel and its corresponding diameter.

Extending this principle, the transducers 114, 116 may be fixedly mounted to the support plate 102 and aligned therewith in a manner which renders their use independent of the radius of curvature of the reactor vessels 104, 106. As shown, although the transducers 114, 116 are arranged at a location other than along the radial axis of the vessels 104, 106, these transducers are aligned such that their respective ultrasonic sensing beams penetrate the vessels at the common point 108 for a predetermined spaced location of the tool 100 with respect to the tangent line 110. In other words, the operation of the transducers 114, 116 is rendered independent of the radius of curvature of the vessel 104, 106 by aiming the ultrasonic sensing beams emitting therefrom to intersect the previously noted imaginary line indicated on the surface of the vessel and parallel to the longitudinal axis of the vessel when the support plate 102 is positioned at a predetermined spaced location relative to such imaginary line.

As shown, the angle x formed between the sensing beam emitted from the transducer 116 and the tangent line 110 is the same for either vessel 104 or vessel 106. Likewise, the angle y formed between the ultrasonic sensing beam emitted from the transducer 114 and the tangent line 110 is independent of the radius of curvature of the vessel 104 or vessel 100. As likewise noted with respect to transducer 112, a plurality of transducers other than those identified as transducers 114, 116 may be employed in accordance with the thus far described principles. In employing such principles, a plurality of transducers can be arranged and aligned with respect to the support plate 102 for operation independent of the radius of curvature of the vessels 104, 106, provided the ultrasonic sensing beams emitted from such transducers are aimed to penetrate a portion of such vessels lying substantially along the imaginary line which is parallel to the longitudinal axis of the vessels, that is, intersecting a plane containing the radial axis of such vessels at the imaginary line when the tool 100 is positioned at a predetermined spaced location relative to the examination surface.

Referring to FIG. 1, transducers TR 0 through TR 4 are mounted to the support plate 102 for inspection of the nozzle safe end weld volumes. In particular, transducers TR 0, TR 1, and TR 2 are fixedly mounted to the support plate 102 along its longitudinal axis, which axis is to be arranged during utilization of the tool in a plane containing the radial axis of the tubular object or vessel being inspected. As to transducers TR 3 and TR 4, such transducers are mounted to the left and right, respectively, of the longitudinal axis of the support plate 102. These transducers TR 3 and TR 4, unlike transducers 114, 116, as shown in FIG. 4, are aligned for emitting an ultrasonic sensing beam outwardly in the direction of the arrows indicated, that is, away from the imaginary line on the vessel being inspected.

It is required that these transducers TR 3 and TR 4 have a refracted angle of about 41°. As a consequence, in order to achieve such a refracted angle with the ultrasonic sensing beams being emitting toward the imaginary line, it would be required that these transducers be spaced apart a relatively large distance which would necessitate increasing the overall size of the support plate 102 and emcumbering it with its associated disadvantages. Therefore, these transducers, TR 3 and TR 4, have been directed outwardly so as to minimize the required size of the support plate 102. As a consequence, transducers TR 3 and TR 4 are removedly mounted to the support plate 102 as their orientation angle is sensative to the radius of curvature and dependent upon the diameter of the nozzle being inspected.

In addition, the orientation angle of transducers TR 3 and TR 4 require adjustment dependent upon whether the nozzle being inspected is an inlet nozzle or an outlet nozzle, as these nozzles have a different radius of curvature and a corresponding different diameter. Notwithstanding the requirement for adjusting the orientation angles of transducers TR 3 and TR 4, the transducers TR 0 through TR 4 for inspecting the nozzle safe end welds are clustered in a compact array having their ultrasonic sensing beams directed at a common weld volume for simultaneous inspection thereof by all the transducers. The common weld volume being simultaneously inspected at any one time by transducers TR 0 through TR 4 is generally less than the entire weld volume for the nozzle safe end weld. In this manner, the transducers TR 0 through TR 4 are simultaneously utilized to inspect a common weld volume while the tool 100 is incremented in predetermined steps for inspecting adjacent weld volumes of the nozzle safe end weld until the entire weld volume has been examined. In inspecting the nozzle safe end welds of a 172 inch diameter nuclear reactor vessel for which the tool 100 as shown in FIG. 1 has been designed, the support plate 102 is positioned such that transducer TR 0 is spaced five inches from the surface of the nozzle being examined.

Transducers TRL 0 and TRL 00 are used independent of each other and are fixedly mounted to the left and right, respectively, of the longitudinal axis of the support plate 102. Transducer TRL 0 is used for inspecting ligament areas where the top flange has six inch stud holes, while transducer TRL 00 is used for inspecting ligament areas where the top flange has seven inch stud holes. As the ligament areas represent planar portions between the stud holes of the top flange, there is obviously no radius of curvature to be taken into consideration when performing the ultrasonic inspection. For this reason, the inspection of the ligament areas by transducers TRL 0 or TRL 00, which are oriented normal to the support plate 102, is independent of the distance between the tool and the ligament area, which distance is typically in the order of six to ten inches using transducer TR 0 as a reference point. It is only required that the support plate 102 be arranged parallel to the plane containing the ligament areas such that the ultrasonic sensing beam emitted from the transducers TRL 0 or TRL 00 be received normal to such plane. To this end, transducers TR 13 and TR 14 are mixedly mounted to the support plate 102 to the left and right, respectively, of its longitudinal axis for ensuring proper plate orientation before use. That is, transducers TR 13 and TR 14 varify the perpendicularity of transducer TR 0, which in turn ensures the perpendicularity of transducers TRL 0 and TRL 00. These transducers, TR 13 and TR 14, are therefore independent of the radius of curvature and corresponding diameter of the vessel when used for ensuring the perpendicularity of transducer TR 0.

Transducers TR 5 through TR 8 are adapted for inspection of the nozzle to vessel weld volume. As shown, transducers TR 5 and TR 6 are arranged along the longitudinal axis of the support plate 102, while transducers TR 7 and TR 8 are mounted to the left and right, respectively, of the longitudinal axis. Transducers TR 7 and TR 8 are fixedly mounted to the support plate 102 and are orientated such that their ultrasonic sensing beams will penetrate that portion of the vessel being examined along the imaginary line such that their orientation angle is independent of the radius of curvature and corresponding diameter of the nozzle or vessel. Although transducers TR 5 and TR 6 are arranged along the longitudinal axis of the support plate 102, these transducers are removedly mounted, as opposed to be fixedly mounted like transducers TR 7 and TR 8, as the taper section of the various nozzles being inspected for different reactor vessels vary. For example, some vessels are not provided with a taper section and therefore the orientation angles for the transducers TR 5 and TR 6 require adjustment for the specific nozzle geometry of the reactor vessel being inspected. However, the use of transducers TR 5 through TR 8 is not dependent upon the radius of curvature of the nozzle and vessel and their corresponding diameter. Based upon the orientation angles disclosed for the transducers TR 5 through TR 8, the support plate 102 is positioned eleven inches from the surface of the vessel being examined, using transducers TR 0 as a reference point, with transducers TR 5 and TR 6 arranged in alignment with the imaginary line lying along the nozzle.

Transducers TR 9 through TR 12 are adapted for inspection of the flange to vessel weld volumes. As these transducers are inspecting a planar surface, in the same manner as transducers TRL 0 and TRL 00, the use of these transducers is independent of the radius of curvature and the corresponding diameter of the vessel. Unlike transducers TR 0 through TR 4 and TR 5 through TR 8, these transducers are not arranged for simultaneous inspection of a common weld volume. That is, transducers TR 9 through TR 12 are arranged for individually inspecting separate weld volumes along a circumferential section of the flange to vessel weld area by being arranged adjacent each other along a substantially straight line, which line is generally at a right angle to the longitudinal axis of the support plate 102. The transducers TR 9 through TR 12 are arranged to have their ultrasonic sensing beams penetrate the top flange of the reactor vessel along a segment of the circumference of the flange at a predetermined radial location. As the radius of the vessel is substantially large, this circumferential segment approximates a straight line. In this manner, the tool 100 is moved radially outward in step wise fashion across the radial extent of the top flange and the tool is further positioned at adjacent circumferential segments for continuous inspection of the flange to vessel weld volume.

Typically, the tool 100 is positioned using transducer TR 9 as a reference point, such that the support plate 102 is arranged 11.5 inches from the top surface of the flange when performing the flange to vessel weld volume inspections. As shown in FIG. 1, the orientation angle of transducers TR 10 through TR 12 vary slightly such that the ultrasonic inspection beams emitted therefrom will penetrate the top flange along the circumferential segment being inspected. From the thus far described arrangement of transducers TR 0 through TR 14, including transducers TRL 0 and TRL 00, only transducers TR 3 and TR 4 are dependent upon the radius of curvature and corresponding diameter of the reactor vessel nozzle being inspected.

Figure 3:
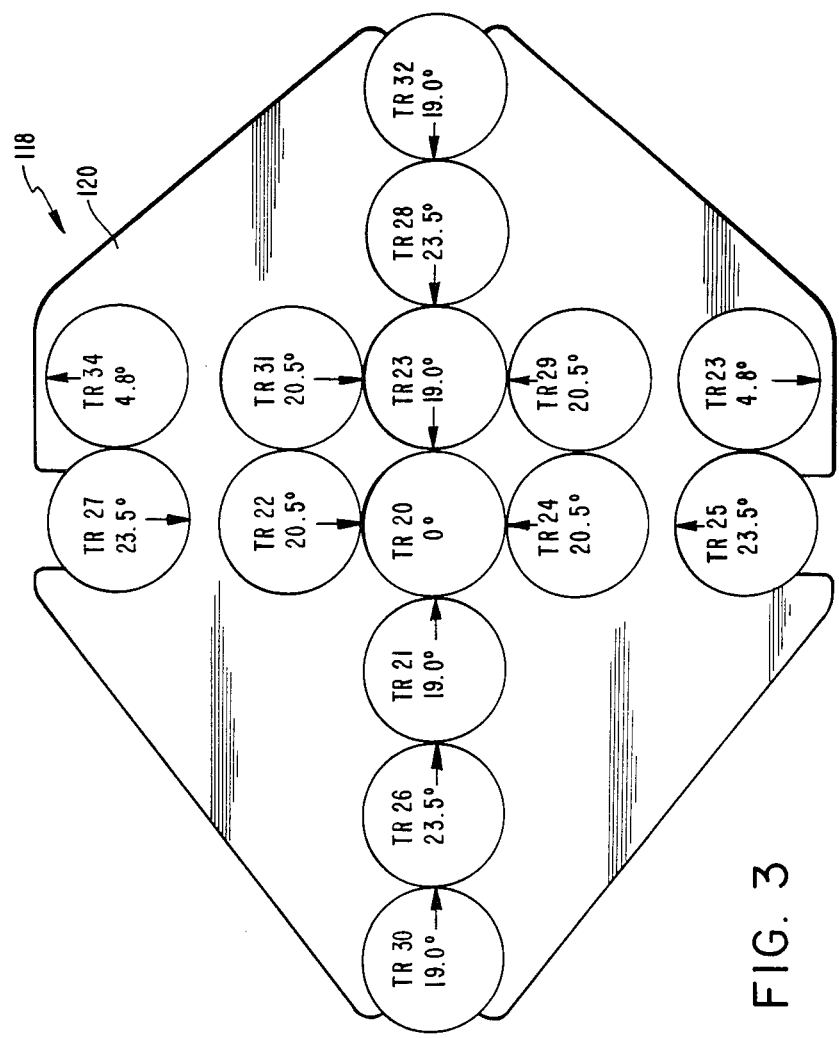
FIG. 3 is a front view of a universal tool constructed similar to that shown in FIG. 1 and adapted for ultrasonic testing of various welds of a reactor vessel at ten year periods.

Referring now to FIG. 3, there will be described the construction of a universal tool generally designated by reference character 118 adapted for conducting circumferential and longitudinal weld volumes examinations at ten year periods. The universal tool 118 is constructed of a triangular shaped support plate 120 measuring about 17 inches in length and 14 inches in width, which is substantially smaller and lighter in weight than the prior art tool which was rectangular in shape measuring 26 inches in length and 18 inches in width. The transducers TR 20 through TR 34 are all used for the inspection of the circumferential and longitudinal welds and are fixedly mounted to the support plate 120. Transducers TR 33 and TR 34 are used to ensure the perpendicularity of transducer TR 20 in the same manner transducers TR 13 and TR 14 are used to ensure the perpendicularity of transducer TR 0 of the universal tool 100.

Figure 2:
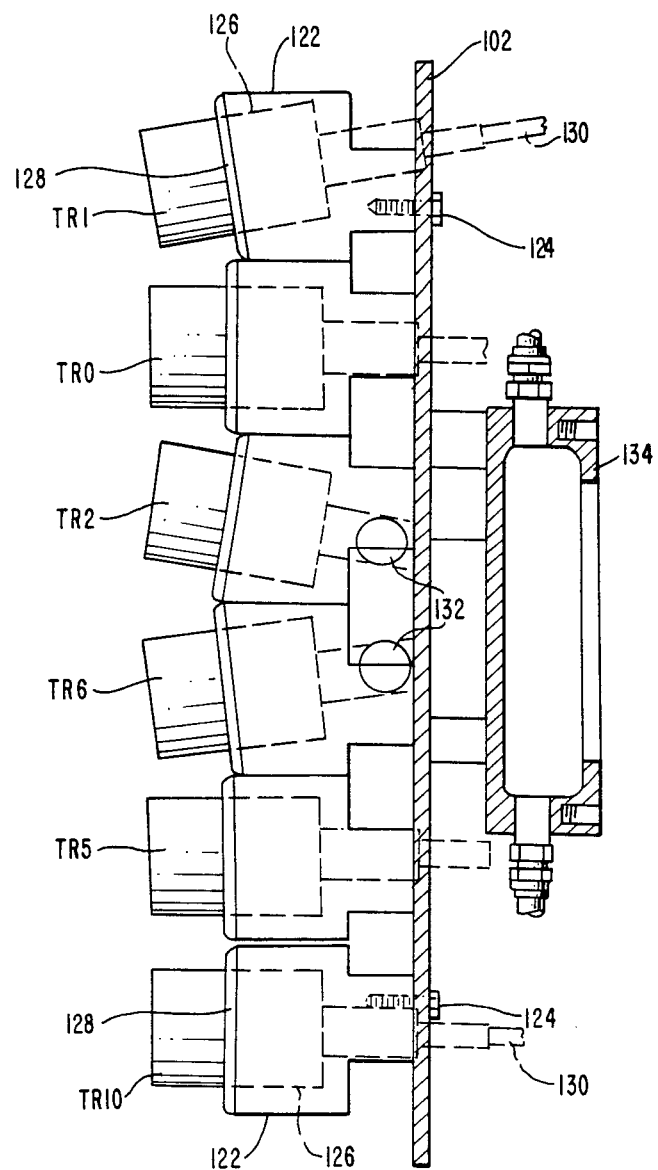
FIG. 2 is a cross-sectional view taken along Line 2—2 of FIG. 1 showing a plurality of individual transducers mounted to the support plate in a fixture.

As shown in FIG. 3, transducers TR 20, TR 21, TR 23, TR 26, TR 28, TR 30 and TR 32 are arranged along the longitudinal axis of the support plate 120, and aimed in the direction of their corresponding arrow as indicated at the designated orientation angles. These transducers TR 20, TR 21, TR 23, TR 26, TR 28, TR 30 and TR 32, are accordingly aligned for emitting their ultrasonic sensing beams to penetrate the surface of the vessel lying along the imaginary line such that the radius of curvature and corresponding diameter of the reactor vessel is not a consideration. As to transducers TR 22, TR 24, TR 25, TR 27, TR 29 and TR 31, such transducers are arranged on either side of the longitudinal axis of the tool 118 and have a respective orientation angle so as to direct their ultrasonic sensing beam at the imaginary line on the vessel and lying within the plane containing the radial axis of the reactor vessel. Accordingly, these transducers likewise may be utilized without changing their orientation angle for reactor vessels having different radii of curvature and corresponding different diameters. As to transducers TR 33 and TR 34, these transducers like transducers TR 13 and 14 are for the purposes of ensuring perpendicularity of transducer TR 20 and accordingly are not dependent upon the radius of curvature of the reactor vessel. The universal tool 118, as shown in FIG. 3, has been designed for conducting inspections of an 11 inch water path when transducer TR 20 is arranged normal to the surface of that portion of the reactor vessel being examined Referring to FIG. 2, the manner of securing the individual transducers to the support plate 102 of the universal tool 100 will now be described. It is to be understood that the universal tool 118 is constructed in a similar manner. A plurality of fixture housings 122 are individually mounted to the support plate 102 by a plurality of bolts 124 extending through the support plate and threadably engaging a portion of the housing. Each housing 122 is provided with a bore 126 arranged at an angle to the support plate 102 corresponding to the orientation angle of the specific transducer to be received therein. For example, the housing 122 adapted for receiving transducer TR 1 is provided with a bore 126 arranged at a downward facing angle of 9.5°. Each of the transducers are secured within their respective housings 122 by means of a clamp assembly 128. The electrical communication lines 130 from each of the transducers extend through the support plate 102 except where a right angle connector 132 is provided at the central portion of the support plate. The connector 132 accommodates the mounting of the universal tool 100 to the G-axis of a manipulator device 134, which device is described and illustrated in the foregoing commonly assigned patents. By use of the manipulator device 134, the universal tools 100, 118 can be manipulated in and around a reactor vessel for inspection of the various weld volumes as mandated by government regulations, that is, the ASME Code, such as top flange to vessel welds, nozzle welds, nozzle safe end welds, ligament areas, circumferential welds and longitudinal welds.

There has thus far been described in accordance with the present invention a universal tool adapted for the inspection of the various weld volumes found in tubular objects such as reactor vessels. In particular, the universal tool, for the most part, allows for such inspection independent of considerations which are normally given to the radius of curvature of vessels having different diameters. The specific embodiment of the universal tools 100, 118, as illustrated in FIG. 1 and FIG. 3 have been designed for a reactor vessel having a diameter of 172 inches. However, the universal tools 100, 118, may be used with reactor vessels of different diameters, such as diameters of 132 inches and 155 inches when taking into consideration the thus described principles of the present invention. As described, those transducers which are not arranged along the longitudinal axis of the universal tool 100, 118, and which do not lie in a plane containing the radial axis of the reactor vessel or nozzle, are oriented such that their ultrasonic sensing beams penetrate that portion of the vessel lying substantially along the imaginary line. It is obvious, that under such circumstances, the universal tools 110, 118 are required to be positioned at a predetermined distance from the examination surface to ensure that these inspection beams penetrate the designated portions to be examined substantially along the imaginary line. For example, in inspecting the nozzle to vessel weld volumes by transducers TR 7 and TR 8, transducer TR 0 is positioned 11 inches from the surface of the nozzle being examined. However, it should be understood, that it may be desired to position transducer TR 0 other than 11 inches from the surface of the nozzle being examined. In this regard, it will be required that the orientation angle of transducers TR 7 and TR 8 be changed, as well as those other transducers employing similar principles of the present invention. In order to determine the correct orientation angles, conventional trigonometric principles are employed, that is, taking into consideration the refractive index of water and the reactor vessel material, as well as the desired incident beam angle and refracted beam angle, the particular orientation of a transducer on the support plate may be determined.

Although the invention herein has been described with respect to particular embodiments, it is to be understood that these embodiments are merely illustrative of the principles and application of the present invention. It is therefore to be understood that numerous modifications may be made in the illustrative embodiments and that other embodiments may be devised without departing from the spirit and scope of the present invention as defined by the appended claims.

What is claimed is:

1. A composite tool for inspecting portions of a plurality of objects for locating defects therein, each of said objects having a longitudinal axis and a different radius of curvature, said tool comprising a support plate, and a plurality of individual sensors mounted to said plate for emitting inspection beams therefrom, said sensors being arranged relative to said plate such that said inspection beams from each of said sensors penetrate a predetermined portion of said object lying substantially along an imaginary line on the surface of said object when said plate is positioned at a predetermined location relative to said line, said imaginary line lying in a plane containing said longitudinal axis of said body whereby the inspection of said predetermined portion of said object by said sensors is independent of the radius of curvature of said object being inspected.

2. The tool of claim 1 wherein said sensors each comprise an ultrasonic transmitter and receiver.

3. The tool of claim 1 wherein said sensors are arranged in a group, said sensors in said group adapted for inspection of a common predetermined portion of said object.

4. The tool of claim 3 wherein said sensors are arranged in a plurality of groups, a first number of said groups being positioned and aligned at predetermined angles to said plate to permit simultaneous inspection by said beams of a respective predetermined portion of said object.

5. The tool of claim 4 wherein a second number of said groups are aligned at predetermined angles to said plate to permit separate inspection of locations within a predetermined portion of said object.

6. The tool of claim 4 wherein said groups of individual sensors are positioned relative to one another so as to minimize the size of said plate.

7. The tool of claim 1 wherein a first number of said sensors are fixedly mounted to said plate.

8. The tool of claim 7 wherein a second number of said sensors are removably mounted to said plate.

9. The tool of claim 1 wherein said object comprises a nuclear reactor vessel.

10. The tool of claim 1 wherein said sensors are arranged along an axis of said plate, said axis during the inspection of said object lying in a plane containing said longitudinal axis of said object and said imaginary line when said plate is positioned at said predetermined location relative to said object for inspection thereof.

11. The tool of claim 10 wherein said sensors are aligned for directing said inspection beams to fall within said plane.

12. The tool of claim 1 wherein said sensors are arranged along an axis of said plate, said axis during the inspection of said object lying outside said plane containing said longitudinal axis of said object and said imaginary line when said plate is positioned at said predetermined location relative to said object for inspection thereof.

13. The tool of claim 12 wherein said sensors are aligned for directing said inspection beams to intersect said plane at said imaginary line.

14. The tool of claim 12 wherein said sensors are arranged in a group, a first number of individual sensors of said group lying within said plane while a second number of individual sensors of said group lying outside said plane.

15. The tool of claim 14 wherein said sensors are arranged in a plurality of groups, a first number of individual sensors of each of said groups lying within said plane while a second number of individual sensors of each of said groups lying outside said plane.

16. A tool having an array of ultrasonic transducers for rendering an ultrasonic inspection of a plurality of objects having cylindrical portions of different curvatures while maintaining said transducers at the same orientation with respect to one another, comprising a support plate for supporting said transducers, a row of individual transducers disposed along a line in said support plate for emitting and receiving a plurality of ultrasonic beams disposed along a plant which is substantially orthogonal to said support plate, a plurality of transducers on either side of said row for transmitting and directing an ultrasonic beam through a focal line in said beam plane which is parallel to the row of ultrasonic transducers, and positioning means for aligning said beam plane with a radial plane of one of said cylindrical objects and for positioning said focal line on the surface of said object.

17. A tool as described in claim 16, wherein said support plate is formed from high strength aluminum.

18. A tool as described in claim 16, wherein said plurality of transducers are substantially symmetrically arranged with respect to said row of individual transducers.

19. A tool as described in claim 16, wherein at least one of said transducers in said row transmits and directs an ultrasonic beam which is orthogonally disposed with respect to said support plate.

20. A tool as described in claim 19, further including at least first and second additional transducers on either side of said row, respectively, for transmitting and directing at ultrasonic beam which is orthogonally disposed with respect to said support plate, wherein the information generated by said first and second transducers is used to remotely control the positioning means.

21. A process for ultrasonically inspecting a plurality of objects having cylindrical portions of different curvatures with a fixed array of ultrasonic transducers which are maintained in the same orientation with respect to one another as said different cylindrical portions are inspected, comprising the steps of:
(a) generating a plurality of ultrasonic beams along a common plane;
(b) generating a plurality of other ultrasonic beams which converge on said common beam plane along a common line;
(c) aligning said beam plane with a radial plane of said cylindrical portion of a selected one of said objects while positioning said focal line on a portion of the surface of said object, and
(d) monitoring the resulting reflections of ultrasonic beams.

* * * * *